(12) United States Patent
Lockhart et al.

(10) Patent No.: US 9,267,165 B2
(45) Date of Patent: Feb. 23, 2016

(54) ASSAYS AND KITS FOR DETECTING PROTEIN BINDING

(75) Inventors: David J. Lockhart, Del Mar, CA (US); Patrick Parvis Zarrinkar, San Diego, CA (US); Daniel Kelly Treiber, San Diego, CA (US)

(73) Assignee: DiscoveRx Corporation, Fremont, CA (US)

( * ) Notice: Subject to any disclaimer, the term of this patent is extended or adjusted under 35 U.S.C. 154(b) by 1315 days.

(21) Appl. No.: 11/895,307

(22) Filed: Aug. 23, 2007

(65) Prior Publication Data

US 2008/0058219 A1 Mar. 6, 2008

Related U.S. Application Data

(63) Continuation of application No. 10/873,835, filed on Jun. 21, 2004, now abandoned, which is a continuation-in-part of application No. 10/406,797, filed on Apr. 2, 2003, now abandoned, and a continuation-in-part of application No. 10/214,654, filed on Aug. 7, 2002, now Pat. No. 7,112,435, said application No. 10/406,797 is a continuation-in-part of application No. 10/115,442, filed on Apr. 2, 2002, now abandoned.

(60) Provisional application No. 60/480,587, filed on Jun. 20, 2003.

(51) Int. Cl.
 *C12Q 1/48* (2006.01)
 *G01N 33/566* (2006.01)
 *G01N 33/543* (2006.01)
 *G01N 33/577* (2006.01)

(52) U.S. Cl.
 CPC .............. *C12Q 1/485* (2013.01); *G01N 33/543* (2013.01); *G01N 33/566* (2013.01); *G01N 33/577* (2013.01); *G01N 2333/912* (2013.01); *G01N 2500/02* (2013.01)

(58) Field of Classification Search
 None
 See application file for complete search history.

(56) References Cited

U.S. PATENT DOCUMENTS

| | | | |
|---|---|---|---|
| 5,096,815 A | 3/1992 | Ladner et al. | |
| 5,198,346 A | 3/1993 | Ladner et al. | |
| 5,223,409 A | 6/1993 | Ladner et al. | |
| 5,403,484 A | 4/1995 | Ladner et al. | |
| 5,437,981 A | 8/1995 | Deger et al. | |
| 5,498,538 A * | 3/1996 | Kay et al. | 506/2 |
| 5,536,814 A | 7/1996 | Ruoslahti et al. | |
| 5,571,698 A | 11/1996 | Ladner et al. | |
| 5,693,489 A | 12/1997 | Studier et al. | |
| 5,766,905 A | 6/1998 | Studier et al. | |
| 5,837,242 A | 11/1998 | Holliger et al. | |
| 5,885,793 A | 3/1999 | Griffiths et al. | |
| 6,162,613 A * | 12/2000 | Su et al. | 435/15 |
| 6,172,197 B1 | 1/2001 | McCafferty et al. | |
| 6,245,760 B1 | 6/2001 | He et al. | |
| 6,265,169 B1 | 7/2001 | Cortese et al. | |
| 6,326,155 B1 | 12/2001 | Maclennan et al. | |
| 6,602,977 B1 | 8/2003 | Ljungqvist et al. | |
| 6,630,335 B1 * | 10/2003 | Kapeller-Libermann | 435/194 |
| 6,897,019 B1 | 5/2005 | Greenberg | |
| 7,060,506 B2 | 6/2006 | Craig | |
| 2002/0123071 A1 | 9/2002 | Knudsen et al. | |
| 2002/0164667 A1* | 11/2002 | Alitalo et al. | 435/7.23 |
| 2002/0197606 A1 | 12/2002 | Craig | |
| 2003/0194749 A1 | 10/2003 | Wandless et al. | |

FOREIGN PATENT DOCUMENTS

| | | | | |
|---|---|---|---|---|
| WO | WO 96/02000 | 1/1996 | | |
| WO | WO 96/41865 | 12/1996 | | |
| WO | WO 9734137 A2 * | 9/1997 | | |
| WO | WO 01/18234 * | 3/2001 | ............... | C12Q 1/00 |
| WO | WO 01/18234 A1 | 3/2001 | | |
| WO | WO 0118234 A1 * | 3/2001 | | |
| WO | WO 01/53479 A2 * | 7/2001 | ............. | C12N 15/10 |
| WO | WO 01/57069 | 8/2001 | | |
| WO | WO 01/98330 | 12/2001 | | |
| WO | WO 03/005036 | 1/2003 | | |
| WO | WO 03/050308 | 6/2003 | | |

OTHER PUBLICATIONS

Frantz et al. Biochemistry 37: 13846-13853, 1998.*
Pargellis et al. Natural Structural Biology 9(4): 268-272, published Mar. 18, 2002.*
Ma et al. (2001) "Rapid determination of adenoviral vector titers by quantitative real-time PCR" J Virol Methods 93(1-2):181-8.*
Broyles et al (2002) "PCR-Based Method for Detecting Viral Penetration of Medical Exam Gloves" Journal of Clinical Microbiology 40(8):2725-2728.*
Jayne et al. (2003) "Use of Real-Time Polymerase Chain Reaction to Identify Cell- and Tissue-Type-Selective Peptides by Phage Display" American Journal of Pathology 162(5):1419-1429.*
Zozulya et al., "Mapping signal transduction pathways by phage display," Nature Biotechnology, vol. 17, Dec. 1999, pp. 1193-1198, XP002936629.
U.S.P.T.O, Non-final Office Action dated May 17, 2005 for U.S. Appl. No. 10/115,442.
U.S.P.T.O, Final Office Action dated Mar. 31, 2006 for U.S. Appl. No. 10/115,442.

(Continued)

*Primary Examiner* — Tracy Vivlemore
*Assistant Examiner* — Karen S Weiler
(74) *Attorney, Agent, or Firm* — Bozicevic, Field & Francis LLP; David J. Aston

(57) ABSTRACT

The invention provides methods for determining the interactions between phage-displayed proteins and test molecules. The phage-displayed proteins are contacted with a reference moiety in the presence and absence of a test molecule; the behavior of the phage-displayed proteins as a function of concentration of the test molecule permits calculation of the binding affinity of the phage-displayed protein for the test molecule.

22 Claims, 1 Drawing Sheet

(56) References Cited

OTHER PUBLICATIONS

U.S.P.T.O, Advisory Action dated Aug. 24, 2006 for U.S. Appl. No. 10/115,442.
U.S.P.T.O, Non-final Office Action dated Dec. 18, 2006 for U.S. Appl. No. 10/115,442.
U.S.P.T.O, Non-final Office Action dated Aug. 16, 2006 for U.S. Appl. No. 10/406,797.
U.S.P.T.O, Final Office Action dated Apr. 10, 2007 for U.S. Appl. No. 10/406,797.
U.S.P.T.O, Non-final Office Action dated Apr. 7, 2006 for U.S. Appl. No. 10/873,835.
U.S.P.T.O, Final Office Action dated Oct. 24, 2006 for U.S. Appl. No. 10/873,835.
U.S.P.T.O, Advisory Action dated Feb. 26, 2007 for U.S. Appl. No. 10/873,835.
U.S.P.T.O, Non-final Office Action dated May 1, 2009 for U.S. Appl. No. 11/982,389.
U.S.P.T.O, Final Office Action dated Feb. 19, 2010 for U.S. Appl. No. 11/982,389.
Lowman, H.B. "Bacteriophage Display and Discovery of Peptide Leads for Drug Development" (1997) vol. 26: 401-424.
Condron et al., An analysis of sequences stimulating frame shifting in the decoding of gene 10 of bacteriophage T7 Nucleic acid Res. 19 (20) 5607-12 (1991).
Condron et al., Frame shifting in gene 10 of bacteriophage T7 J. Bacteriol. 173 (21) 6998-7003 (1991).
Sipley et al., Bacteriophage T7 morphogenesis and gene 10 frame shifting in *Escherichia coli* showing different degrees of ribosomal fidelity Gen. Genet. 230 (3) 376-84 (1991).
Pope et al., In vitro selection of a high affinity antibody to oestradiol using a phage display human antibody library Immunotech. (1996) 209-217.
Rosenberg, A et al., T7 Select Phage display system: A powerful new protein display system based on bacteriophage T7 inNovations 6 (Dec. 1996), p. 1-6.
Vaughan et al., Human antibodies with sub-nanomolar affinities isolated from a large non immunized phage display library Nat. Biotech. (1996) 14 309-314.
Hoogenboom, H. Designing and optimizing library selection strategies for generating high affinity antibodies. Tibtech (Feb. 1997) 15 62-70.
Nilsson, J et al., Affinity fusion strategies for detection, purification, and immobilization of recombinant proteins. Prot. Exp. & Pur. (1997) 11 1-16.
Hoogenboom, H et al., Antibody phage display technology and its applications Immunotech. (1998)4 1-20.
De Haard et al., A large non-immunized human Fab fragment phage library that permits .. J. Biol. Chem. (1999) 274 (26) 18218-18230.

Wycuff et al. Generation of AraC-araBAD promoter-regulated T7 expression system Analytical Biochemistry (2000) 277 67-73.
Chan, S-W et al., "Human recombinant antibodies specific for hepatitis c virus core and envelope E2 peptides from an immune phage display library," *Jour. Gen. Virol.*, Soc. for General Microbiol. Reading, GB, 77:2531-2539 (1996).
Danner, S. et al., "T7 phage display: a novel genetic selection system for cloning RNA-binding proteins from cDNA libraries," *Proc. Natl. Acad. Sci. USA*, 98:12954-12959 (2001).
Knockaert, M. et al., "Intracellular targets of cyclin-dependent kinase inhibitors: identification by affinity chromatography using immobilised inhibitors," *Chem. & Biol.* 7:411-422 (2000).
Legendre et al., "Engineering a regulatable enzyme for homogeneous immunoassays," *Nature Biotech.* 17:67-72 (1999).
Li, C., et al., "Phage randomization in a chrybdotoxin scaffold leads to CD4-mimetic recognition motifs that bind HIV-1 envelope through non-aromatic sequences," *Jour. Peptide Research*, Munksgaard International Publishers, Copenhagen, DK, 57:507-518 (2001).
Lin, S-Y et al., "*lac* repressor binding to non-operator DNA: detailed studies and a comparison of equilibrium and rate competition methods," *J. Mol. Biol.* 72:671-690 (1972).
Nord et al., "Recombinant human factor VIII-specific affinity ligands selected from phage-displayed combinatorial libraries of protein A," *European Journal of Biochemistry* 268:4269-4277 (2001).
Pistillo, M.P. et al., "Molecular characterization and applications of recombinant scFv antibodies to CD152 co-stimulatory molecule," *Tissue antigens*, 55:229-238 (2000).
Tabor et al., "Selective inactivation of the exonuclease activity of bacteriophage T7 DNA polymerase by in vitro mutagenesis," *J. Biol. Chem.* 264:6447-6458 (1989).
Thirumula-Devi, K. et al., "Phage-displayed peptides that mimic aflatoxin B1 in serological reactivity," *Jour. Applied. Microbiol.* 90:330-336 (2001).
Xu et al., "Anti-peptide aptamers recognize amino acid sequence and bind a protein epitope," *Proc. Natl. Acad. Sci. USA* 93:7475-7480 (1996).
Cunningham et al., "Production of an atrial natriuretic peptide variant that is specific for type A receptor," EMBO J., 1994, vol. 13, No. 11, pp. 2508-2515.
Demangel et al., "Combining phage display and molecular modeling to map the epitope of a neutralizing antitoxin antibody," Eur. J. Biochem., 2000, vol. 267, pp. 2345-2353.
Eyers et al., "Use of a drug-resistant mutant of stress-activated protein kinase 2a/p38 to validate the in vivo specificity of SB 203580," FEBS Letters, 1999, vol. 451, pp. 191-196.
Han et al., "Peptides Selected to Bind the Gal80 Repressor Are Potent Transcriptional Activation Domains in Yeast," *J. Biol. Chem.*, 2000, vol. 275, No. 20, pp. 14979-14984.

* cited by examiner

ASSAYS AND KITS FOR DETECTING PROTEIN BINDING

CROSS-REFERENCE TO RELATED APPLICATIONS

This application is a continuation of U.S. Ser. No. 10/873,835 filed Jun. 21, 2004, which is a continuation-in-part of U.S. Ser. No. 10/406,797 filed Apr. 2, 2003, which in turn is a continuation-in-part of U.S. Ser. No. 10/115,442 filed Apr. 2, 2002. U.S. Ser. No. 10/873,835 is also a continuation-in-part of U.S. Ser. No. 10/214,654 filed Aug. 7, 2002 and claims priority to U.S. Ser. No. 60/480,587 filed Jun. 20, 2003. Each of these applications is incorporated herein by reference in its entirety.

INTRODUCTION

Methods to display a wide variety of peptides or proteins as fusions with coat or other proteins of bacteriophage are well known. The original system was disclosed, for example, in U.S. Pat. Nos. 5,096,815 and 5,198,346. This system used the filamentous phage M13 which required that the cloned protein be generated in E. coli and required translocation of the cloned protein across the E. coli inner membrane. Lytic bacteriophage vectors, such as lambda, T4 and T7 are more practical since they are independent of E. coli secretion. T7 phage is commercially available and described in U.S. Pat. Nos. 5,223,409; 5,403,484; 5,571,698 and 5,766,905.

Traditionally, the phage display system has been used to examine the interaction of the phage-displayed peptides with proteins or peptides. An initial important application of phage display, for example, was the production and "evolution" of single chain antibody variable regions which could then be tested for interaction with a specific antigen. The system could be used to develop specific antibodies for a particular antigen.

More recently, it has been found possible to use phage display techniques to explore interactions between proteins or peptides and "small molecules"—i.e., typically synthetic organic molecules which may be useful as pharmaceutical compounds. This technique is described in PCT publication WO01/18234 published 15 Mar. 2001. In one embodiment of this application, the biological targets for known pharmaceuticals can be ascertained by displaying the protein products of cDNA libraries and using a known pharmaceutical as a "handle" for affinity chromatography. The phage display technique has not been, however, applied to the determination of specificity between "small molecules" and multiple proteins or peptides. The phage display technique has also not been applied to the quantitative measurement of binding affinity between "small molecules" and proteins or peptides. "Small molecules" that target particular protein activities have been the focus of the pharmaceutical and biotechnology industry for some time. The existence of numerous proteins with similar structures and/or activities, however, has complicated efforts to utilize small molecules as therapeutic agents because a given molecule is found to bind and interact with more than one protein.

For example, the inhibition of particular protein kinases and phosphatases has been a focus of therapeutic efforts to treat numerous diseases and pathological conditions, including heart disease, cancer, stroke, hypertension, arthritis, and diabetes. Unfortunately, these efforts have resulted in the development of very few small molecules that are able to inhibit a particular protein kinase or phosphatase to the exclusion of other kinases and phosphatases. A study of multiple protein kinase inhibitors showed that only two inhibitors (rapamycin and PD 184352) did not appreciably affect at least one additional protein kinase in a limited survey of the protein kinase family (see Davies et al., *Biochem. J.* (2000) 351:95-105). The authors of the study also noted that "the specificity of protein kinase inhibitors cannot be assessed simply by studying their effect on kinases that are closely related in primary structure." These observations led the authors in part to counsel the use of additional assays, such as the development and use of a drug resistant kinase mutant, to verify that the cellular effects of an inhibitor are due to the targeting of a single protein kinase target (see Eyers, et al., *FEBS Lett.* (1999) 451:191-196). Such assays are necessarily expensive in terms of time, labor and materials as well as difficult in cases where a drug resistant mutant is not readily available.

The desire to obtain acceptably specific inhibitors of protein kinase has also led to the use of protein-small molecule structures derived from co-crystals or modeling studies to study, design and produce more specific inhibitors (see for example Pargellis et al. (Nature Structural Biol. (2002) 9:268-272)). Such approaches are again expensive in terms of time and labor.

Citation of documents herein is not intended as an admission that any is pertinent prior art. All statements as to the date or representation as to the contents of documents is based on the information available to the applicant and does not constitute any admission as to the correctness of the dates or contents of the documents.

SUMMARY OF THE INVENTION

The present invention provides methods and kits for identifying interactions between test molecules and polypeptides. Preferably the polypeptides are displayed on phage and the interactions are evaluated in the presence of reference moieties that are optionally attached to a solid support.

One aspect of the invention is a method for determining the binding affinities of a test molecule to different polypeptides from a set of polypeptides. This method comprises contacting the test molecule to the different polypeptides from the set in the presence of a reference moiety and evaluating the binding of the reference moieties to the polypeptides. This binding interaction identifies the binding properties between the polypeptides and the test molecule.

In another aspect, the invention provides a method of screening libraries of compounds against one or more polypeptides. Typically, groups of test molecules are tested with the polypeptide of interest and once a binding interaction of interest has been identified, the test molecules can be further evaluated individually.

The present invention also provides methods of quantifying the interaction between phage-displayed polypeptides and test molecules. Also are included, business methods for the pharmaceutical development of test molecules evaluated using the techniques described herein. Other aspects include the test molecules and pharmaceutical formulations and therapeutic and/or prophylactic uses thereof.

Kits for performing the assays described herein are also provided. The kits typically comprise of the phage-displayed polypeptides and reference moieties along with instructions for performing the methods described herein.

DISCLOSURE OF THE INVENTION

Figure 1A:
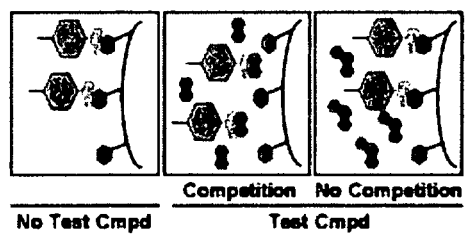
FIGS. 1A, 1B and 1C show a diagrammatic depiction of an embodiment of a method of the invention and results obtained from this method.

The invention is based on the ability to assess the affinity of the interaction, if any, of a test molecule and a phage-displayed polypeptide in the presence of a reference moiety that binds the displayed polypeptide. The test molecule may be considered as a competitor against the reference moiety for binding to the displayed polypeptide. The invention is preferably embodied as a system for assaying the affinities between one or more test molecules and more than one displayed polypeptide in parallel such that the affinity(ies) of said molecule(s) for each polypeptide of a group can be compared. Each polypeptide is individually displayed on phage particles and exposed to both a test molecule at one or more concentrations and to a reference moiety. In one embodiment of the invention, each individually displayed polypeptide is bound to a reference moiety followed by contact with a test molecule at one or more concentrations. The reference moiety may optionally be immobilized, such as by attachment to a solid phase surface. The reference moiety may also be optionally labeled with for example, fluorescence and/or spectroscopic tags. The amount of phage particles bound to, or displaced from, the reference moiety relative to the concentration of the test molecule permits the determination of the affinity of the interaction between the test molecule and the polypeptide. Alternatively, the reference moiety may be labeled with a reporter group, such as a fluorescent probe, that permits alternative readouts of the interaction between the polypeptide and the reference moiety. Fluorescence polarization is a non-limiting example of a method that could be used to detect interactions between the labeled reference moiety and the polypeptide at various concentrations of the test molecule.

In an alternative embodiment, a displayed polypeptide is exposed to an immobilized reference moiety and the reaction is allowed to equilibrate. After washing to remove unbound phage, the reaction is contacted with a test molecule which may elute bound phage particles from the reference moiety. The amount of eluted phage displaying the polypeptide as a function of the concentration of the test molecule is used to determine the affinity(ies) of the polypeptide for the test molecule.

In a third embodiment, a displayed polypeptide is simultaneously exposed to an immobilized reference moiety and a test molecule and the system is allowed to reach equilibrium. After washing to remove unbound phage, the amount of eluted phage displaying the polypeptide at a plurality of concentrations of the test molecule is used to determine the affinity of the polypeptide for the test molecule. Instead of simultaneous exposure, the order of addition of displayed polypeptide, reference moiety, and test molecule may be in any order as long as sufficient time for the system to reach equilibrium is permitted.

The affinity of the interaction between a phage displayed polypeptide and a test molecule as described above may be reflected as binding constants. The binding constants may be used to identify the test molecule(s) as (relatively) specific and/or selective for one or a few of the polypeptides tested or relatively non-specific and/or non-selective due to significant interactions with several or many of the polypeptides tested.

The invention also provides for comparisons of the binding constants, which may be expressed as dissociation or association constants, to identify the test molecule(s) as specific or selective for one or more particular polypeptide.

Therefore, in one aspect, the invention is directed to a method to apply phage display technology, wherein the method comprises simultaneously contacting a phage-displayed polypeptide with a reference moiety immobilized on a solid support and a test molecule at a sufficient concentration to decrease the binding of the displayed polypeptide to the reference moiety. The concentrations of the test molecule necessary to diminish binding of the displayed polypeptide from the reference moiety may be used to determine a dissociation constant ($K_d$) for the test molecule. Preferably, the $K_d$ values for the test molecule and members of a group of polypeptides with similar structures and/or activities are determined in parallel. The resulting $K_d$ values may be compared to identify the test molecule as specific and/or selective for one or more particular polypeptides.

In one aspect of the invention, the binding properties of a test molecule across a set of polypeptides is evaluated. This set of polypeptides may comprise of polypeptides from the same protein family or from different protein families. For example, the binding affinities of a test molecule to the different kinases from the kinase family can be evaluated. Preferably, the reference moiety used is a promiscuous moiety, that is, it binds to more than one member of the set of polypeptides being evaluated. For example, for the kinase family the reference moiety used binds the active ATP site. Suitable reference moieties for evaluating the binding affinities of test molecules to kinases are described herein. In certain embodiments, the test molecules are exposed to one polypeptide at a time from the set of polypeptides to determine the binding affinities. In other embodiments, the test molecule may be exposed to multiple polypeptides simultaneously. In these embodiments, typically, after detection of a positive interaction, the polypeptides are individually evaluated for their binding properties to the test molecule. In preferred embodiments, the reference moiety used across a set of polypeptides is the same.

In another aspect of the invention, libraries of compounds are screened for their binding properties to individual polypeptides or to sets of polypeptides. Multiples compounds may be tested at one time. Typically, if multiple compounds are tested, following a positive interaction, the compounds are individually evaluated for their binding properties.

Typically, the phage expressing a particular polypeptide is exposed to both a reference moiety immobilized on a solid support and a test molecule at one or more concentrations. The test molecule may bind the polypeptide such that binding to the reference moiety is reduced by binding to the test molecule. The test molecule thus competes against binding to the reference moiety to decrease the number of phage associated with the solid support. The phage bound to the solid support at one or multiple concentrations of the test molecule can be eluted, preferably after removal of unbound phage, and enumerated by standard phage titering methods. A decrease in the amount of phage bound to the solid support in the presence of the test molecule identifies the test molecule as a binder of the displayed polypeptide.

Phage displaying a polypeptide may be bound by low or high concentrations of a test molecule that has a high degree of affinity for the polypeptide. High concentrations of a test molecule with low or moderate affinity for the polypeptide are needed to prevent phage association with the reference moiety. Phage displaying a polypeptide that binds to the reference moiety despite high concentrations of the test molecule may be identified as displaying a polypeptide that has no or minimal interactions with the test molecule. Phage-displayed polypeptides which are detectably bound to the immobilized reference moiety in the absence of a test molecule, but which are no longer detectable even at low concentrations of the molecule are identified as high affinity binders to said test molecule. In one embodiment of the invention, a single "high" concentration of the test molecule is used in a primary screen to identify, but not to discriminate between, high, moderate, and low affinity binders. Potential interactions that are identified in the primary screen are assayed again using a plurality of concentrations (used individually) of the test molecule to provide binding data. Preferably, more than 5, 10, 11, 12, or 15 concentrations of the test molecule are used to generate a binding curve that can be fit to an equation that calculates an accurate, rigorous binding constant, such as a $K_d$ value.

Preferably, a group or family of polypeptides with similar structures and/or activities are displayed on phage and used in the practice of the invention. Each polypeptide member of the group or family is expressed on a plurality of phage particles which are contacted with the reference moiety separate from phage particles displaying another member polypeptide. Stated differently, phage clones, displaying the same polypeptide, are individually exposed to test molecules in the practice of the invention. The affinity of a test molecule for each polypeptide of a group or family may then be determined and compared in accordance with the invention to identify the strength of interactions among all the individual polypeptides of the group or family for the test molecule. The strength of the interactions may be used as an indicator of the specificity and/or selectivity of the test molecule for individual polypeptide(s) of the group or family and to identify new small-molecule/protein interactions that may be important for drug development where the displayed polypeptide(s) have been identified or hypothesized to be targets for drug development. The invention thus provides for the identification of a molecule as being specific and/or selective for one or more members of a group or family relative to other members of the group or family.

A group of polypeptides is preferably composed of members with related activity and/or structure. Non-limiting examples of family members include proteins that catalyze the same type of enzymatic reaction or the same type of enzymatic reaction. In some embodiments of the invention, a family of polypeptides is that from a single cell type, tissue source, or organism. Polypeptides for the practice of the invention may be naturally occurring or mutant forms thereof, including a mutant form of a naturally occurring protein which is associated with disease. Mutant forms that are not found in nature may also be used in the practice of the invention. In another aspect, the test molecule to be contacted with a group or family of polypeptides displayed on phage is a candidate activator or inhibitor of one or more members of the group or family. Therefore, embodiments of the invention provide for the determination of specificity and/or selectivity of a modulator molecule for one or more polypeptides of a group or family. When a family of related enzymatic activities from a single source, such as human protein kinases, is used in the practice of the invention, the specificity and/or selectivity of a candidate molecule, such as a protein kinase inhibitor, may be readily determined. The candidate molecule may be identified as specific for one, or a few, protein kinase(s) to the exclusion of other members of the family.

By use of the methods of the invention, test molecules that non-specifically bind to a group or family of related polypeptides are readily identified. Test molecules that bind to multiple members of a family of polypeptides may also be identified. Similarly, test molecules that specifically or selectively bind one or a few members of a group or family are readily identified along with their corresponding binding constants, such as their $K_d$. Therefore, in other aspects, the invention is directed to methods to identify non-specific test molecules which would otherwise have required more extensive experimentation to detect. The identified non-specific test molecules may in turn be advantageously used in the practice of the invention as reference moieties to which a phage displayed group or family is bound in the practice of the invention. Particularly preferred reference moieties bind a variety of proteins or peptides with similar structures and/or activities with moderate or high affinity. The invention also allows the identification of previously unknown interactions that may suggest novel uses for a test molecule, or derivatives thereof.

Methods to determine the dissociation constant of a test molecule with members of a group or family of polypeptides comprise assessing the binding of the displayed proteinaceous member to a reference moiety in the presence of various concentrations of the test molecule. The number of phage bound to the reference moiety as a function of the test molecule concentration may be plotted on a graph and the $K_d$ is calculated by fitting the curve to an appropriate binding equation. In some embodiments, the concentration of test molecule at which binding of the phage-displayed member to the reference moiety is reduced by 50% is equal to the $K_d$ for the interaction between the displayed protein and the test molecule.

The invention also provides for the formulation of dissociation constant information into a database or other tabular form for ease of use and subsequent analysis. In one form, the information may be in a table wherein individual polypeptides are represented by columns, and the identities of various test molecules are represented by rows, of the table. Each cell of the table contains the dissociation constant information for the combination of a particular polypeptide and a test molecule. Each row of the table thus reflects the specificity profile of a test molecule for all the polypeptides tested and readily permits the identification of the test molecule as binding one or a few polypeptides as opposed to promiscuously binding to multiple polypeptides. Such a table preferably contains the results from the use of multiple polypeptides with a single or multiple reference moieties, although multiple tables of this type may be combined as desired. Computer-based clustering methods can be used to represent the data in such a way that the binding profile of every test molecule and every polypeptide can be related to one another. In this clustered representation of the data, polypeptides that tend to bind the same test molecules are placed close to one another, whereas polypeptides that tend to bind different test molecules are placed far from one another. Likewise, test molecules that bind common members of a group or family of polypeptides are placed close to one another, and test molecules that have dissimilar binding profiles are place far from one another. This clustered representation of the data is more informative, and thus preferred in some circumstances over a raw "tabular" format, because it provides potential predictive insight that can drive new drug discovery efforts.

The invention is also directed to methods to discover the effects of structural alterations in a test molecule on the affinity for a polypeptide. A test molecule identified as binding one or more members of a group or family of polypeptides may be used as the lead compound for the preparation of additional compounds with similar structures to the lead compound. The library of compounds, including the lead compound, may be individually used with a group or family of polypeptides to identify whether the differences in structure between the lead compound and derivatives affect the specificity of binding to members of the group or family. The library of compounds may also be used to determine whether and how the changes in structure affect the affinity of the lead compound for members of the group or family. Methods of using information concerning the effect of changes in structure to determine the structures of additional compounds to be prepared may also, therefore, be used.

The lead compound may also be used as the reference moiety by immobilizing it on a solid support. Members of the phage displayed group or family are contacted with both the immobilized lead compound (as the reference moiety) and other compounds, including, but not limited to those derived from the lead compound.

The occurrence of toxicity or unwanted side effects of a test molecule may be predicted based on a determination of specificity as described herein. A test molecule that is found to bind only one or a few polypeptides would be predicted as unlikely to cause significant toxicity or side effects when used in a subject. This follows because the test molecule is less likely to bind, and thus affect, similar polypeptides in the cells and tissues of the subject. On the other hand, a test molecule that is relatively non-specific and binds many polypeptides is more likely to cause toxicity or side effects upon use in a subject. The determination of the likelihood of toxicity or undesirable side effects in a subject is preferably conducted with respect to a plant or animal subject, more preferably a human subject.

As used herein, a "test molecule" refers to the chemical entities such as, but not limited to, a protein, organic or inorganic molecule, carbohydrate, or other compound to which a polypeptide is tested for binding. A "test molecule" of the invention includes pharmaceuticals and candidate pharmaceuticals which are natural products or which are prepared synthetically. Non-limiting examples include polyketides, steroids, the compounds found in the U.S. Pharmacopoeia, and the products of combinatorial chemical synthesis. Candidate pharmaceuticals include molecules for which no function is known, but which have structural similarity to known compounds with one or more known functions. "Polypeptide" refers to any protein or peptide, naturally occurring or synthetic (including fragments, portions, and mutants of a protein or peptide) composed of amino acids linked by peptide (amide) bonds. The amino acids may be naturally occurring or synthetic, including D- and L-forms of amino acids.

The polypeptide, preferably displayed on a phage particle, is exposed to a "reference moiety" that is preferably immobilized on a solid support. Immobilization of the reference moiety may be by a variety of means, and standard means of covalently or non-covalently coupling a molecule to solid supports are well known in the art. Non-limiting examples include the use of linker molecules, crosslinkers such as glutaraldehyde, and biotin/avidin interactions. An example of the latter is with the use of biotin covalently coupled to a molecule and avidin bound to a solid support. The solid support itself can take any convenient form, typically a culture dish or plate or bottle, a well of a multi-well culture dish or plate, a bead, a column containing particles to which a molecule is immobilized, or a planar surface containing the immobilized molecule. Other non-limiting examples of a solid support include agarose, polystyrene or other polyvinyl compounds, and magnetic beads.

The reference moiety may be coupled covalently to the support or may be noncovalently bound by a system which permits the release of the entire complex containing a bound phage particle and reference moiety. For example, a solid support derivatized with N-hydroxysuccinimide can be used to couple covalently a carboxylic acid function of a reference moiety. For such coupling, elution of the bound phage would rely on competition with excess reference moiety or other change of conditions. However, advantageously mild elution conditions may be used when the reference moiety is coupled covalently only to a linker ligand which is itself noncovalently coupled to the solid support. Under those circumstances, the complex can be eluted in a manner not specific to the reference moiety—for example, by supplying an excess of the linker.

A non-limiting example of the use of a linker ligand is a system wherein the reference moiety is covalently bound to biotin which serves as a linker ligand to noncovalently adsorb to an avidin derivatized solid support. After washing with buffer to remove non-bound phage, the phage/reference moiety complex can be removed by treating the solid support with excess biotin. Similarly, the reference moiety may be covalently coupled to other linkers such as polyhistidine which noncovalently associates with nickel chelates (on a solid support) permitting removal or elution using excess polyhistidine, or can be coupled to glutathione which associates with a glutathione-S-transferase system coupled to the support or vice versa. A large number of such ligand linkers which can be covalently bound to a reference moiety but noncovalently bound to a derivatized solid support are known, thus permitting a variety of non reference moiety-specific elution protocols.

In a preferred embodiment of the invention, a biotin-streptavidin interaction is used to immobilize a reference moiety on magnetic beads. While this interaction is not covalent, it is of such high affinity ($K_d=10^{-15}$ M), that it is treated as essentially covalent under many circumstances. The reference moiety is covalently linked to biotin (directly or via a linker) which is bound to streptavidin coated magnetic beads. After contact with the member(s) of a group or family of polypeptides and a test molecule, the beads are isolated and the phage particle displayed polypeptide(s) are eluted. A variety of elution conditions may be used. Non-limiting examples include elution with a soluble version of the reference moiety that lacks biotin; elution with a detergent solution, such as one containing SDS, which denatures the polypeptide(s) to disrupt binding to the reference moiety; and elution with a protease containing solution to cleave the displayed polypeptide from the phage. The first elution example is preferred to elute bound phage particles based on binding to the soluble reference moiety. In alternative embodiments of the invention, other versions of streptavidin, such as monomeric avidin with a lower affinity for biotin, are used such that elution with free biotin may be used. The eluted phage may be quantified by any appropriate means, including, but not limited to, standard phage titering methods, such as a plaque forming assay or by quantitative PCR (QPCR).

While the above discussion details particularly mild elution conditions which may be advantageous under some conditions, it is not a necessary feature of the invention. Covalent bonding of a reference moiety to a solid support is also practical and elution can be effected by methods appropriate to this system.

Essentially any molecule may be used as a reference moiety of the invention, although molecules that bind to a site that affects the activity or functionality of a polypeptide are preferred. Reference moieties are preferably molecules that bind with high affinity to many members of a group or family being assayed. Stated differently, preferred reference moieties bind almost all members of a group or family of polypeptides, although not necessarily with the same affinity. More preferred for use as a reference moiety is a molecule known to bind, or be competitive for binding, to an active site of a polypeptide, or to other known sites of pharmacological relevance.

Where a group or family comprises polypeptides with enzymatic activity, the reference moieties are preferably substrate or product analogs. As a non-limiting example, the reference moiety may be an ATP substrate analog where the proteins or peptides are capable of binding ATP, such as in the case of protein kinases or other ATP dependent enzymatic activities. Alternatively, the reference moiety may be a modulator, such as an activator or inhibitor of said enzymatic polypeptides. A non-limiting example for protein kinases is the use of the inhibitor staurosporine as a reference moiety.

Exemplary compounds for use as a reference moiety in the practice of the invention with a group of protein kinases include, but are not limited to, staurosporine; protein kinase inhibitors, including those in Davies et al. SB 203580, SB 202190, SU6668, SU5416, SU6597, SU6663, SU6561, SU 4984 and SU5402 as discussed by Laird et al. (Cancer Res. (2000) 60:4152-4160) and Krystal et al. (Cancer Res. (2001) 61:3660-3668) and Mohammadi et al. (Science (1997) 276: 956-960); substituted 3-[(3- or 4-carboxyethylpyrrol-2-yl) methylidenyl]indolin-2-ones inhibitors of VEGFR, FGFR, and PDGFR receptor tyrosine kinases as discussed by Sun et al. (J. Med. Chem. (1999) 42:5120-5130); pyridinylmidazole compounds such as VK-19911 as discussed by Wilson et al. (Chem. & Biol. (1997) 4:523-431); VK19577 as discussed by Whitmarsh et al. (Mol. Cell. Biol. (1997) 17:2360-2371); BIRB 796 and SK&F 86002 as discussed by Pargellis et al. (Nature Structural Biol. (2002) 9:268-272); N-pyrazole, N'-aryl urea based inhibitors as discussed by Regan et al. (J. Med. Chem. (2002) 45:2994-3008); purvalanol A, B and related compounds as discussed by Knockaert et al. (Chem. & Biol. (2000) 7:411-422) and Gray et al. (Science (1998) 281: 533-538); and compounds commercially available from Sigma/Aldrich, such as, but not limited to, bisindolylmaleimide I hydrochloride (GF 109203X), indirubin 3'monoxime, lavendustin A, olomoucine, Ro 31-8220 (bisindolylmaleimide IX), Ro 32-0432, and roscovitine. These compounds may of course also be used as a test molecule when the phage displayed polypeptide is bound to another compound as the reference moiety. Preferred reference moieties for the practice of the invention with protein kinases are staurosporine, purvalanol B, SU5402, Gleevec® (imatinib mesylate), SU6668, Iressa® (ZD1839 or gefitinib), PD-173955, and SB202190, which bind to multiple kinases disclosed herein. Preferred reference moieties bind with high affinity ($K_d$ less than or equal to 1 µM) to a plurality of polypeptides having similar structure and/or function.

In one embodiment of the invention, the reference moiety may be the small molecule used as "bait" in U.S. patent application Ser. No. 09/653,668, filed 1 Sep. 2000, hereby incorporated in its entirety as if fully set forth. As presented in that application, the "bait" is used to identify phage displayed polypeptides that bind to it followed by sequencing the nucleic acid molecule encoding the polypeptide(s) or other means of identifying the polypeptide(s). The identified polypeptide(s) and proteins or peptides having similar structure and/or activities, may be all or part of a group or family of polypeptides. In another embodiment of the invention, the phage used to display a polypeptide of the invention is that disclosed in U.S. patent application Ser. No. 10/214,654 filed Aug. 7, 2002, hereby incorporated in its entirety as if fully set forth.

The choice of a group or family of polypeptides with similar activities and/or structures may be as desired by a skilled user of the invention. The invention is most advantageously applied to those polypeptides with similar activities, such as those catalyzing the same type of enzymatic reaction. A group comprising proteins with protein kinase activity or the binding characteristics of protein kinases is a particularly preferred embodiment of the invention. The number of estimated protein kinases and variants thereof in a higher eukaryotic cell is estimated to be greater than five-hundred and members of this family are involved in regulating many cellular functions. Due to structural and functional similarities between protein kinases, the use of a protein kinase inhibitor raises the issue of the inhibitor targeting more than one kinase. The present invention provides an efficient means to determine the selectivity of such an inhibitor among members of a group or family of kinase proteins used in the practice of the invention. The selectivity profiles provided by use of the present invention may also reveal novel interactions with other pharmacologically relevant members of a group or family that suggests new uses for a molecule.

The invention is not, however, limited to applications with protein kinase activities. Groups of other transferase activities, including acyltransferase, glycosyltransferase, nitrogen transferring, and sulfur transferring activities may also be used in the practice of the invention. Similarly, groups of the other enzymatic activities (oxidoreductase, hydrolase, lyase, isomerase, ligase) as classified by the Nomenclature Committee of the International Union of Biochemistry and Molecular Biology (NC-IUBMB) may be used in the practice of the invention. Groups of polypeptides may be viewed as a library of known polypeptides that are used in the practice of the invention. The invention may also be practiced with the use of a group of polypeptides that have similar binding characteristics for a substrate or substrate analog without necessarily the same enzymatic activity. A non-limiting example is kinases and other ATP dependent enzymes, such as an ATP dependent protease, which bind ATP and ATP analogs.

In preferred embodiments of the invention, a family of polypeptides having the same or similar activity, and from a human cell, tissue, or organism, is used in the practice of the invention. Polypeptides (including fragments thereof) from a variety of sources may be used. Non-limiting examples include single tissues such as brain, liver, stomach, prostate tissue, breast tissue, and the like from a variety of mammals, particularly humans. Non-limiting examples also include cell containing material from other organisms, such as yeast, invertebrates, plants, or prokaryotes. Polypeptides may be those from a source considered "normal" or disease free as well as those from an organism exhibiting, or a tissue associated with, an "abnormal" condition or disease, such as inflammation, tumor growth, hypertrophy, diabetes, Alzheimer's disease, and the like. Non-limiting examples include mutant proteins that are associated with disease or drug-resistance in an organism, such as the mutant forms of ABL kinase believed to play a role in some leukemias. While the protein kinase inhibitor Gleevec is used to target the ABL kinase effectively, acquired mutations in ABL preclude Gleevec binding to result in resistance to Gleevec use. The instant invention may be used with the mutant forms of ABL kinase, or the mutant forms of other polypeptides that give rise to disease or drug resistance, to identify additional inhibitors that selectively bind them.

Particularly preferred for use herein are polypeptides with protein kinase activity. Non-limiting examples of protein kinase activities for use in the present invention are MAPK12, MAP2K6, GPRK7, CDK7, CDK9, PCTK1, JNK1α/ MAPK8α, JNK1β/MAPK8β, JNK2a/MAPK9a, JNK3/ MAPK10, CDK2, DAPK2, DMPK, NEK2, PAM, PAK6, KIAA1048 (BIKE-like), STK16, RS6KA2, RS6KA3, RS6KA5, LCK, PRKAA2, CSK, DAPK3, PRKACA, PAM (murine), PAK3, PAK7, BIKE, STK3 (murine) STK4, STK15/STK6(BTAK)/AURORA2, PIMI, PIM2, CAMK1, LOC57118 (CamK1-like), CamKIG, CamK2A, CamK2B, CamK2D, CamK2G, CamKKI, CamKK2, FGFR1, and PDGFRβ, all of which bind staurosporine with a dissociation constant ranging from less than 0.1 to less than 5 µM. Other exemplary kinases include casein kinase 1, gamma 1; MAPK14/p38; STK18; STK25; VEGF receptor 2 (VEGFR2); ABL and mutants thereof; BRAF and mutants thereof; EGFR and mutants thereof; ERBB2; and ERBB4. Other exemplary protein kinases are provided in Manning et al. (Science 2002 298(5600):1912-34), which is hereby incorporated by reference as if fully set forth. While the invention may be practiced with a group or family of polypeptides from a single species, it may also be practiced with a group or family of polypeptides including members from another species. As a non-limiting example, a group or family of human kinases may also include one or more murine, rodent, or other mammalian or primate kinase, for comparison and/or in place of a human kinase which is not known or available.

The nucleotide sequences encoding a polypeptide used in the practice of the invention may be accessed from publicly available databases such as GenBank or RefSeq. Genes are identified based upon keywords or sequence homology. PCR primers may then be designed and the coding sequences amplified from cDNA using standard PCR protocols. PCR amplicons may be directly cloned into T7 bacteriophage, or other display systems, for display and use as described herein.

Alternatively, polypeptides with ligand binding activity, such as cellular receptors that bind ligands, and optionally have a catalytic function, may also be used in the practice of the invention.

Polypeptides of a group or family may be selected by any desirable means, including searches of nucleic acid or protein sequence databases (such as, but not limited to GenBank, RefSeq, and Swiss-Prot) by use of keywords or sequences identified as related to, or a consensus of, a particular activity. PCR primers may then be designed for the amplification of sequences encoding the selected polypeptides from cDNA libraries using conventional PCR methods. The PCR amplicons are preferably designed to be readily cloned into a bacteriophage vector for protein display on the phage particle surface. Alternative means for the preparation of coding sequences, such as by conventional cloning with detection by a small probe sequence followed by subcloning into a phage vector, may also be used. Total gene synthesis by standard chemical coupling methods may be used as well.

The phage-displayed protein or peptide is produced as a fusion polypeptide with a coat protein characterizing the phage. The displayed, non-phage protein can be coupled to the C-terminus or the N-terminus of the coat protein characteristic of the phage. In a preferred embodiment, the non-phage protein to be studied is coupled to the C-terminus of the coat protein in order to avoid instances wherein a stop codon contained in the non-phage protein or peptide interrupts translation before the nucleotide sequence encoding the coat protein occurs. Of course the use of appropriate cloning or PCR strategies can remove stop codons from known sequences prior to fusion with a phage protein. Preferably the displayed polypeptide is either monovalent or an active single subunit able to bind a reference moiety for the practice of the invention. A variety of phages may be used in the practice of the invention, including lytic bacteriophage vectors (e.g. lambda, T4 and T7), filamentous phage (e.g. M13), and other vector means including viruses.

In one aspect, the present invention utilizes phage particles displaying known individual protein members of a group or family. Homogenous phage particles displaying a protein are exposed to, or contacted with, a reference moiety immobilized on a solid support, such as a magnetic bead. Thus each assay well contains an immobilized reference moiety that binds to phage particles that display a protein member of a group or family. The phage particles in each well are also exposed to, or contacted with, a concentration of a test molecule. The phage are prevented from binding the solid support when there is binding to the test molecule. The number of phage remaining bound to the solid support at various concentrations of the test molecule is determined by eluting the support-bound phage and then performing standard phage titering assays (plaque assays) or quantitative PCR-based methods, such as QPCR. Alternatively, phage could be labeled with a reporter group that permits sensitive spectroscopic detection. A non-limiting example would be a fluorescent label that can be detected with high sensitivity fluorimetry.

In some embodiments, in a microtiter plate or dish format, all wells may contain the same immobilized reference moiety while each column of wells contains phage particles displaying the same protein. Each row of wells contains a different test molecule and/or a different concentration of a test molecule. Thus, information concerning the strength of interaction with the test molecule used in the practice of the invention can be matched to the corresponding protein family member. Many alternative formats are possible, including use of multiple reference moieties used on a single plate, and use of multiple phage particles and competing molecules. In one embodiment, one or more "pool" of test molecules may be contacted with phage particles displaying members of a group or family to increase the likelihood of a decrease in phage binding to the reference moiety. A "pool" is subsequently separated into the individual competitor molecules to identify the one or more test molecules that decrease phage binding to the reference moiety.

The strength of interaction information may be summarized as identifying a test molecule to
1) be unable to inhibit phage displayed proteins from binding to a reference moiety under the conditions and concentrations used;
2) bind a phage displayed protein strongly, and thus able to inhibit the phage particles from binding the reference moiety even at low concentrations of test molecule;
3) bind a phage display protein moderately or weakly, and thus requiring high concentrations of the test molecule to inhibit binding of the phage particles to the reference moiety;
4) bind phage particles displaying a plurality of different proteins, and thus the molecule is (relatively) non-selective; or
5) bind phage particles displaying from one to five different proteins, and thus the molecule is (relatively) specific.

The identification of phage displayed proteins that bind selectively or non-selectively to a test molecule is useful in many contexts. Non-limiting examples include the identification of specifically binding proteins as potential cellular targets of a molecule. If the test molecule is a natural product or a known pharmaceutical, this may identify a cellular target of the molecule. Proteins that bind a test molecule may also be classified based upon the interaction, which may reveal molecular aspects of side effects seen with the use of the molecule as a pharmaceutical. This knowledge permits the design of new molecules, new formulations and co-treatment regimens to alleviate such effects.

The identification of novel specific interactions for a pharmaceutical or known compound, such as a member of a combinatorial library, to a polypeptide also permits the identification of new uses or applications of the pharmaceutical or known compound. The identification of a non-specific compound is also useful to provide an additional reference moiety for the practice of the invention.

In one aspect, the invention provides a method to assess the binding of a phage-displayed polypeptide to a test molecule. The method comprises contacting said polypeptide with a reference moiety immobilized on a solid support in the presence of a test molecule, and assessing the amount of the phage-displayed polypeptide bound to said solid support. Preferably, the invention is practiced via detection of phage that remains associated with said solid support. The identity of the displayed polypeptide is preferably known and used as part of a plurality of phage-displayed polypeptides that are individually contacted with said solution. Such a plurality preferably comprises more than 5, more than 10, more than 20, more than 50, more than 100, or more than 150 displayed polypeptides, although the invention is not limited by the number of polypeptides in the plurality. The test molecule is preferably at a concentration of less than about 30 µM, less than about 25 µM, less than about 20 µM, less than about 15 µM, less than about 10 µM, less than about 5 µM, less than about 1 µM, less than about 0.5 µM, less than about 0.1 µM, less than about 0.05 µM, less than about 0.01 µM, less than about 0.005 µM, or less than about 0.001 µM.

Screening Tool

The present invention is advantageously applied toward the parallel screening of multiple molecules for binding and selectivity to a group or family of polypeptides. As described herein, each member of a group or family of polypeptides is displayed on phage particles that may bind to a solid support through interaction between the displayed polypeptide and a reference moiety linked to the support. The phage, when exposed to the reference moiety, is also contacted with test molecules to be screened for binding to the displayed polypeptides. The ability of the test molecule(s) to inhibit phage from binding the reference moiety by competition is used to identify the test molecule(s) as binding the polypeptide(s) displayed on said phage.

The use of various concentrations of each test molecule permits the calculation of a binding constant $K_d$ for interactions between the test molecule and the displayed polypeptide(s). The $K_d$ is defined as the concentration of a test molecule whereby 50% of the polypeptide or phage displayed polypeptide is released from the reference moiety in comparison to the absence of the test molecule. The $K_d$ may be a calculated value based upon a comparison of bound phage versus concentration of a test molecule, such as by a plot of the two variables in a graph.

The test molecules that bind a given polypeptide may be classified as strong, moderate and weak binders of the polypeptide. In many instances, but not necessarily all, strong (high affinity) binders would have $K_d$ values of <1 µM and moderate binders would have $K_d$'s in the range of about 1-about 100 µM. Weak binders would have $K_d$ values of more than about 100 µM. However, these ranges will vary depending on the nature of the interaction sought. The advantage of the method of the invention is that relative strength of binding by a plurality of different polypeptides to individual test molecules can be efficiently determined and used as a screening tool to identify a test molecule as selective for one or more of the polypeptides.

To screen for a molecule's selectivity, the $K_d$ values for a given test molecule with respect to the group of polypeptides assayed may be compared to identify any differences. A test molecule may bind a particular polypeptide with a $K_d$ from about 1-about 10 nM or lower and thus be selective for said polypeptide if other polypeptides tested only bind with a $K_d$ of about 1-about 100 µM or higher. Alternatively, a test molecule may bind a plurality of polypeptides with a $K_d$ of about 0.1 to about 5 µM and thus be non-selective for any one of the polypeptides.

The relative difference in $K_d$ is important because in situations where a test molecule selective for a polypeptide is contacted with multiple polypeptides in combination, the concentration of the molecule may be controlled to result in only selective binding with little to no binding to the other polypeptides. Such situations regularly occur in the use of pharmaceutical agents, which can be administered in precise dosages to provide a particular concentration to permit selective binding by protein(s) with a sufficiently low $K_d$.

By using a known reference moiety and a plurality of displayed polypeptides that bind to it, the possibility of "false positives," such as in situations where the displayed polypeptides are unknown, is diminished or essentially eliminated. A "false positive" may be due to some distortion of the reference moiety due to immobilization or other spurious binding of a polypeptide to the reference moiety. A "false positive" may be identified by the use of the reference moiety in soluble form, without a chemical linker, to compete with binding by the immobilized form. If the soluble form of the reference moiety does not compete, the binding of a polypeptide to the immobilized form is an artifact.

When there is no test molecule in solution to be screened in, displayed polypeptides will bind to the reference moiety based upon their affinities therefor. As the concentration of a test molecule is increased, a polypeptide that is a high affinity binder is readily identified because they are released from the solid support at low concentrations of the test molecule. Thus, a polypeptide that binds the solid support which can not be recovered from the solid support in the presence of low concentrations of test molecule is identified as not a high affinity binder to the polypeptide.

Moderate and low affinity binders can also be identified by the methods of the invention. While high concentrations of test molecule can successfully compete with the immobilized reference moiety for binding to a displayed polypeptide, a low concentration of test molecule will not be sufficient to displace a moderate or low affinity polypeptide from binding to the solid support. Thus a medium concentration of test molecule may be used to release a moderate affinity polypeptide from the solid support while not being of a sufficiently high concentration to release low affinity polypeptides from the support. At high concentrations of test molecules, both polypeptides which bind strongly and those which bind moderately or weakly to test molecule are successfully competed away from binding to the solid support.

The invention may also be practiced via sequential or parallel contacting of displayed polypeptides immobilized on a solid support via binding to a reference moiety (in a solution containing no test molecule) with 1) a solution containing a low concentration of test molecule, 2) a solution containing a medium concentration of test molecule, and 3) a solution containing a high concentration of test molecule permitting the sequential release of polypeptides with high, moderate, and low affinities, respectively, for said test molecule.

As noted above, the practice of the invention also permits the identification of the selectivity of the test molecules for the individual polypeptides that are displayed. Molecules that are identified as selective for releasing only one or a few of a group or family of polypeptides from the solid support are less likely to have a deleterious effect (such as side effects upon use of the molecule as a therapeutic agent) due to binding interactions with other polypeptides of the group or family. If such a molecule is also a high affinity binder, then the ability to control binding to other polypeptides can be further controlled by administration of a low amount of the compound as a therapeutic to reduce its concentration in vivo and minimize binding to other polypeptides.

Molecules that are identified as non-selective for releasing many or all of a group or family of polypeptides from the solid support are more likely to have a deleterious effect upon use of the molecule as a therapeutic agent because of the high likelihood of spurious effects mediated by binding to other proteins and peptides in vivo. But such molecules may be preferred for use as an immobilized reference moiety in subsequent embodiments of the invention for the screening of additional test molecules as described herein. Preferably, such molecules are identified via an initial screen with a known modulator (activator or inhibitor) of a group or family of polypeptides so that the molecules are competitors of the known modulator. These molecules may have a high, moderate, or low affinity for the group or family of polypeptides because regardless of the affinity, the molecule can still be used as the reference moiety in methods as disclosed herein. Preferably, such non-selective molecules have a high or moderate affinity to facilitate the screening of additional test molecules for molecules with high affinity and selectivity to the proteins or peptides.

Because phage-displayed polypeptides with a high affinity for a test molecule in solution can be identified by comparing retention to the solid support in the presence of low concentrations of the test molecule in comparison to retention in the absence of the molecule, only two determinations are required. Alternatively, a plurality of concentrations of test molecule may be used in parallel. The plurality may be of 5 or more, 10 or more, or 15 or more concentrations.

As to the quantitation of "low" and "high" concentrations of test molecule, the numerical value of these concentrations will depend on the actual values of high and low affinity binding in the context in which the phage display screening takes place. As a non-limiting example, a pharmaceutical agent may be known or believed to act by binding and inhibiting a particular cellular polypeptide target. The agent may also be known or suspected to bind other cellular polypeptides to result in undesirable side effects. Because the affinity and selectivity of the agent for various cellular proteins or peptides is unknown, it is often presumed that the agent has a higher affinity for the particular cellular protein or peptide target. But the value of the dissociation constants that describes the interaction between the agent and its particular cellular protein or peptide target and other cellular proteins or peptides is unknown.

Applying the instant invention to the above scenario as a non-limiting example, a plurality of possible cellular proteins and/or peptides may be exposed to a reference moiety as disclosed herein in the presence of different concentrations of said agent where "high" and "low" concentrations are defined empirically. A "low" concentration might arbitrarily, then, be defined as 1-10 nM. If this concentration fails to disrupt the retention of the proteins or peptides on the solid support, the concentration would be increased to, for example, 10-20 nM, and thus incrementally to 20-50 nM, 50-100 nM, 100 nM-1 µM, 1 µM-10 µM and so on. The appropriate concentration would be identified as that which results in substantial lack of retention of one or more phage-displayed protein or peptide. A "low" concentration or concentration range would then be selected from the ranges below that which was selected as "high." Preferably a range at least 10-100 fold lower would be selected.

If the presumption of high affinity binding by the agent to the particular cellular protein or peptide target is correct, that target should remain unassociated with the reference moiety at low concentrations of said agent. The ability to release other cellular proteins or peptides, whether at low or high concentrations, can be used to confirm or identify these other proteins or peptides as potential mediators of unwanted side effects associated with the undesirable side effects of clinically using said agent.

Alternatively, the agent may be used as described above to identify other proteins or peptides as potential targets of the agent. A disease condition or indication that is associated with an identified protein or peptide may thus be one that can also be treated clinically by use of said agent. Notably, the dissociation constant that can be determined for said agent relative to said identified protein or peptide may also be used to provide an estimation of the in vivo concentration of said agent for use during therapy.

In another embodiment, the invention may simply be to find a phage-displayed polypeptide which binds with a predetermined affinity for a particular molecule.

The methods of the invention may also be practiced in a qualitative format to approximate the dissociation constant between a test molecule and a displayed polypeptide. A rough estimate can be obtained by determining the minimum concentration of test molecule required to prevent a polypeptide from binding to a solid support as described herein. For example, if the polypeptide under consideration appears no longer to be bound to the support at a concentration of 1 µM, this suggests that the $K_d$ is less than, or equal to, that amount. If a 10 µM concentration is required, but the polypeptide is still bound at a test molecule concentration of 1 µM, the $K_d$ is putatively less than 10 µM but more than 1 µM.

Quantitative Embodiments of the Invention

The conditions of the disclosed methods are important in order to provide the correct quantitative results. One might assume that the concentration of a test molecule to prevent a fixed proportion of the phage from binding a reference moiety would be dependent on the value of the $K_d$ for the interaction between the reference moiety and the displayed polypeptide ($K_{ref}$). Also, in a large excess of phage-displayed protein, the test molecule would not necessarily displace phage already bound to parental molecule, but rather could bind to the excess phage.

Thus, the invention is preferably conducted based on certain testable assumptions wherein it can be shown that the concentration of test molecule that reduces the binding to an immobilized reference moiety molecules by 50% is equal to the $K_d$ for the molecule. The assumptions and conditions are as follows:

First, the concentration of the phage displayed protein must be less than the $K_d$ for the test molecule. Second, the concentration of the immobilized reference moiety must be less than or approximately equal to the $K_{ref}$.

It is straightforward to provide conditions for the assay wherein these assumptions are met. The concentration of phage-displayed protein in the assay is kept quite low, typically less than 1 nM; when very tight binders are encountered, the phage is diluted to a lower concentration. Thus, there is no excess of phage-displayed protein.

The apparent $K_d$ for the test molecule will depend on the $K_{ref}$ for the immobilized reference moiety only when the concentration of immobilized reference moiety is greater than the $K_{ref}$. Thus, in the assays of the invention, typically, the concentration of immobilized reference moiety ranges from 3 nM-300 nM which is generally in the range of $K_{ref}$. If there is any doubt that the concentration of the immobilized reference moiety is in fact less than its $K_{ref}$, the exposure to test molecule can be performed at two concentrations of the immobilized reference moiety to ensure consistency. It is particularly important to test these assumptions when high affinity test molecules are being studied. The validity of these assumptions is tested for every member of the profiling panel of displayed polypeptides before screening assays with test molecules proceed.

When these assumptions are valid, competitive binding between a test molecule and a reference moiety can be described by the following equation:

$$f/f_0 = K_{comp}/(K_{comp} + [comp])$$

where f is the fraction of phage bound to the immobilized reference moiety in the presence of test molecule; $f_0$ is the fraction bound in the absence of test molecule; $K_{comp}$ is the equilibrium dissociation constant ($K_d$) for the interaction between the phage-displayed protein and the test molecule; and [comp] is the concentration of the test molecule. At 50% competition, $f/f_0 = 0.5$, and $K_{comp} = $ [comp].

If the foregoing assumptions are not valid, the apparent $K_d$ for the test molecule as determined by the assay will be overestimated—i.e. the binding to the phage is actually tighter than it appears from the assay. Again, if there is doubt, the assays can be performed at more than one concentration of the immobilized reference moiety to ensure that the assumptions are met.

The above approach of the invention has several advantages. The screened test molecules do not need to be immobilized, and the assay is amenable to scale-up and is quantitative. The assay also benefits from the sensitivity of the phage binding assay, which is significantly greater than that of many traditional binding assays, where it is difficult to detect binding when the concentration of reference moiety is less than or equal to $K_{ref}$. The affinity of the test molecule binders can be discerned from the assay itself. In some embodiments, the phage-based approach described herein employs low polypeptide concentrations (pM), which permits Kd measurements into the pM range.

The ability to assess test molecule specificity rapidly and broadly makes possible the systematic determination of binding profiles for compounds at all stages of development. Screening compound libraries against an entire panel of polypeptides can increase the rate of finding test compounds with desirable activities. Once promising lead compounds have been identified, a rapid feedback loop between medicinal chemistry and specificity assessment provides multi-dimensional structure-binding relationships that can accelerate parallel optimization of potency and specificity. For compounds at later stages of development, profiling against a large panel of polypeptides can identify previously unrecognized interactions with valuable targets that may broaden the compounds' applications. The assays described herein help broaden the application of the family-based approach by simply making it more practical, efficient and cost-effective.

Therapeutic and Prophylactic Uses

The methods described herein have numerous applications in the drug development process. The methods may be used to identify new uses of known drugs, to identify new drugs, for example, from libraries of compounds, and to develop drugs with desired biological activities. In preferred embodiments, the test molecules that are evaluated using the methods described herein are developed into pharmaceutical compositions for therapeutic uses. The present invention also includes the test molecules identified and/or developed using the techniques described herein, analogs, derivatives, metabolites, prodrugs, and pharmaceutically acceptable salts thereof, and pharmaceutical formulations and therapeutic and/or prophylactic uses thereof.

The present invention also includes business methods for developing the test molecules analyzed with the methods described herein for pharmaceutical purposes. In certain embodiments, following the identification of binding properties for a test molecule, preclinical studies are performed on the test molecule, including non-cellular, cellular, and whole animal studies. The test molecule may optionally be chemically modified to improve potency and/or efficacy or to improve toxicity profile or improve bio-availability. The test molecule is preferably formulated into suitable pharmaceutical formulations. The pharmaceutical formulations typically undergo clinical trials and are preferably marketed for therapeutic and/or prophylactic purposes. Typically, the therapeutic and/or prophylactic purposes are related to the binding properties identified using the techniques described herein. The binding experiments of the present invention, the preclinical tests, clinical trials, and marketing may be done by the same party or by multiple parties.

The pharmaceutical compositions for treatment of various diseases comprise the test molecules as an active ingredient in combination with one or more pharmaceutically suitable carrier. The pharmaceutical compositions of the present invention may further comprise other therapeutically active ingredients.

The present invention provides methods, pharmaceutical compositions, and kits for the treatment of an animal. The term "animal" or "animal subject" as used herein includes humans as well as other mammals. The subject invention further provides methods of treating various diseases in a subject suffering therefrom comprising administering to the subject an effective amount of the test molecule, disclosed herein, and a pharmaceutically suitable carrier. The test molecules used in therapeutic applications would be dependent on the condition being treated.

The term "treating" and its grammatical equivalents as used herein includes achieving a therapeutic benefit and/or a prophylactic benefit. By therapeutic benefit is meant eradication, amelioration, or prevention of the underlying disorder being treated or the eradication, amelioration, or prevention of one or more of the physiological symptoms associated with the underlying disorder such that an improvement is observed in the patient, notwithstanding that the patient may still be afflicted with the underlying disorder. For a prophylactic benefit, for example, the compositions described herein may be administered to a patient at risk of developing a particular disease or to a patient reporting one or more of the physiological symptoms of that disease, even though a diagnosis of the disease may not have been made.

The pharmaceutical compositions of the present invention include compositions wherein the test molecules described herein are present in an effective amount, i.e., in an amount effective to achieve therapeutic and/or prophylactic benefit. The actual amount effective for a particular application will depend on the patient (e.g. age, weight) the condition being treated; and the route of administration. Determination of an effective amount is well within the capabilities of those skilled in the art, especially in light of the disclosure herein.

The effective amount for use in humans can be determined from animal models. For example, a dose for humans can be formulated to achieve circulating and/or gastrointestinal concentrations that have been found to be effective in animals.

The dosages of the test molecules in animals will depend on the disease being, treated, the route of administration, and the physical characteristics of the animal being treated. In some embodiments, the dosage levels of the test molecules for therapeutic and/or prophylactic uses can be from about 1 µg/day to about 10 gm/day.

Preferably, the test molecules used for therapeutic and/or prophylactic benefits can be administered alone or in the form of a pharmaceutical composition. The pharmaceutical compositions comprise the test molecules, one or more pharmaceutically acceptable carriers, diluents or excipients, and optionally additional therapeutic agents. For example, the test molecules of the present invention may be co-administered with other active pharmaceutical agents depending on the condition being treated. This co-administration can include simultaneous administration of the two agents in the same dosage form, simultaneous administration in separate dosage forms, and separate administration. In the separate administration protocol, the test molecules and the other pharmaceutical agent may be administered a few minutes apart, or a few hours apart, or a few days apart.

The test molecules can be administered by injection, topically, orally, transdermally, rectally, or via inhalation. Suitable oral formulations include powder, tablet, capsule, solution, or emulsion. The effective amount can be administered in a single dose or in a series of doses separated by appropriate time intervals, such as hours.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Suitable techniques for preparing pharmaceutical compositions of the test molecules described herein are well known in the art.

Exemplification of the Invention as an Illustrative Protocol

Cleared lysates containing a single displayed polypeptide are prepared by infecting log phase ($A_{600}$~0.7) *E. coli* BLT 5615 cells grown in 2×YT medium with a T7 phage clone (M.O.I.~0.05) encoding said polypeptide as a fusion with a coat protein. The infected cells infected with phage encoding each polypeptide are shaken at 325 rpm at 32° C. until the lysate has cleared. The lysates are then aliquotted into individual 2 ml flip top tubes and spun in a microfuge at full speed for 10 minutes. The cleared supernatants are removed and used in the form of "lysate cocktails." The final "lysate cocktail" solutions to be tested contains 0.645× cleared lysate, 0.2× Sea block blocking agent buffer (Pierce #37527 Sea block/1% BSA/0.05% Tween 20, abbreviated SBTB); 1% BSA; 0.5% Triton X-100; and 0.05% Tween 20.

Polystyrene plates containing immobilized reference moiety ("bait') are prepared as follows. As a non-limiting example, four plates (3 polystyrene flat bottomed; 1 polypropylene round bottomed) are prepared. These plates are blocked with 2001 µl SBTB per well.

Dynabeads™ M280 (Streptavidin (Dynal #602.10)) are resuspended by shaking and swirling; the beads are suspended at 10 mg/ml, as described in the next paragraph, and 0.4 mg are used per assay well. The beads are washed 3 times and resuspended in 1×PBS/0.05% Tween 20 (PBST) to 10 mg/ml and distributed to 2 ml tubes. The biotinylated reference moiety is added to the tubes at a molar ratio of 0.025-0.25:1 (reference moiety:biotin-binding capacity), mixed and incubated on the rotator for 30 min at room temperature. Biotin is then added to all tubes at a molar ratio of 2:1 (biotin:biotin-binding capacity) and the tubes are incubated for another 30 min on the rotator.

The polystyrene plates prepared above, without removal of SBTB, are then supplied with the beads at 40 µl of beads per well. The plates containing the beads are shaken briefly at 700 rpm (wash 1), followed by pelleting, decanting, and another wash with shaking with SBTB (wash 2), followed by a third wash where the beads are shaken for >15 min. in SBTB.

200 µl of each lysate cocktail is added to individual wells of a polypropylene plate containing 1 µl of a test molecule in buffer or DMSO at a specified concentration. A control well containing buffer or DMSO lacking test molecules is also used. The lysate cocktail/test molecule mixture is then allowed to bind said beads via interactions between the displayed polypeptide and said reference moiety. The number of wells containing an individual lysate cocktail depends on the number of test molecules, and the number of different concentrations of each molecule, to be assessed. The plates are shaken at 700 rpm for 1 hour at room temperature. The reactions are optionally transferred to a fresh blocked 96-well polystyrene plate and the beads are pelleted, decanted, and 150 µl of SBTB/0.5% Triton X-100 (SBTBT) is added with re-suspension of the beads by shaking at 700 rpm for 5-10 seconds. The beads are washed (optionally three times) with 150 µl of SBTBT. On the fourth wash, the beads are transferred to a fresh blocked polystyrene 96-well plate.

Wells containing each displayed polypeptide are then contacted with a solution containing a concentration of the soluble reference moiety (non-biotinylated) and optionally shaken at 700 rpm at room temperature for 30 minutes. The solution effects an elution of bound phage from the beads. The beads are pelleted and the eluate (solution) from each well is titered for the number of eluted phage by any known or appropriate means.

While the above has been described in the context of a single phage clone, a plurality of clones, each preferably displaying one member of a group or family, may be used as described above but in a multiplex format in the practice of the invention as disclosed herein. Moreover, the invention is not limited to the buffer conditions disclosed above but may rather be practiced with a variety of suitable buffering and assay conditions. In the multiplex format, typically multiple polypeptides are evaluated simultaneously for their binding to one or more test molecules. The multiple polypeptides can belong to the same family of polypeptides or may belong to different families. In one example of a multiplex format, more than one polypeptide, one or more reference moieties, and one or more test molecules are tested together. Preferably, the reference moiety binds more than one polypeptide. In other embodiments, reference moieties that bind one polypeptide from the multiple polypeptides being evaluated is used. In the multiplex format, preferably multiplex qPCR is used to evaluate the results. Also, multiple test molecules may be tested at the same time with one or more than one polypeptide. This is particularly useful when screening large number of test molecules for their binding properties with one polypeptide or a family or polypeptides. Different sets of test molecules can be screened. When it is determined that one or more sets of test molecules show the desired interaction, these sets of test molecules can be further evaluated to determine which members of the set exhibits the desired properties.

Unless defined otherwise all technical and scientific terms used herein have the same meaning as commonly understood to one of ordinary skill in the art to which this invention belongs. The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning:

A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Primers, oligonucleotides and polynucleotides employed in the present invention can be generated using standard techniques known in the art.

EXAMPLES

Test Molecule-Kinase Interactions

Human kinases expressed as fusions to T7 bacteriophage particles and a small set of immobilized ligands that bind to the ATP site of one or more kinases were used. The kinases used in the assays can be viewed as fusion proteins that are tagged in a way that facilitates expression, purification and detection. The tags of the fusion proteins rendered the attached protein amplifiable and amenable to reliable and sensitive detection.

Kinases were cloned in a modified version of the commercially available T7 select 10-3 strain (Novagen and see U.S. patent application Ser. No. 10/214,654 filed Aug. 7, 2002). The head portion of each phage particle includes 415 copies of the major capsid protein, and in this system approximately one to ten of these are kinase fusion proteins. The N-terminus of the kinase was fused to the C-terminus of the capsid protein. The fusion proteins were randomly incorporated, and therefore distributed across the phage head surface. T7 phage replication leads to lysis of the bacterial host, and lysates containing phage-displayed kinases were used directly in the assay.

The immobilized small molecule ligands used to build the assays bind the kinases with high affinity ($K_d$<1 µM), and were amenable to attachment of biotin without disrupting binding. For the assay, phage-displayed kinases and immobilized ATP site ligands were combined with the compound to be tested (FIG. 1A). If the test compound binds the kinase and directly or indirectly occludes the ATP site, it competes with the immobilized ligand and prevents binding to the solid support. If the compound does not bind the kinase, phage-displayed proteins are free to bind to the solid support through the interaction between the kinase and the immobilized ligand. The competing 'test' molecules do not need to be linked, immobilized or chemically modified in any way. The results are read out by quantitating the amount of fusion protein bound to the solid support, which is accomplished with by either traditional phage plaque assays or by quantitative PCR (qPCR) using the phage genome as a template. Both methods can be used to accurately detect and quantitate as few as tens of phage-displayed protein molecules.

Assay for p38 MAP kinase.

Phage-displayed p38 protein and an immobilized ligand that binds the p38 ATP site were used. To produce phage-displayed p38, the coding region for p38α was cloned into the phage genome in-frame with the gene encoding the major T7 capsid protein. As an immobilized ligand we chose SB202190, a pyridinyl imidazole. SB202190 binds the p38 ATP site with high affinity, has a hydroxyl group suitable for biotin attachment at a position that is solvent accessible in the p38 complex, and can still bind p38 when attached to a solid support. Biotin with a flexible linker was chemically attached to SB202190 and the biotinylated compound immobilized on streptavidin-coated magnetic beads.

Figure 1B:
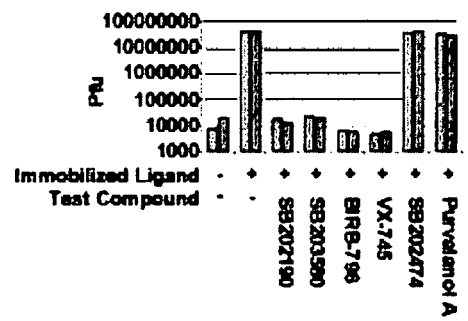
Figure 1C:
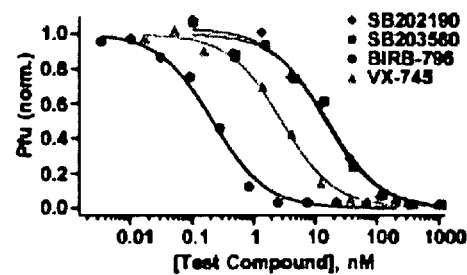

Phage-displayed p38 was found to bind to beads on which SB202190 had been immobilized, but not to beads lacking the ligand (FIG. 1B). Phage with no displayed protein did not bind to beads with or without SB202190. Binding to the solid support is therefore dependent on both the immobilized ligand and on the displayed kinase. Six compounds were tested for the ability to compete with the interaction between p38 and immobilized SB202190: SB202190 (without biotin modification); SB203580 (a pyridinyl imidazole closely related to SB202190) (Table 1); SB202474 (a pyridinyl imidazole that does not bind p38); BIRB-796 (Table 1); VX-745 (Table 1); and purvalanol A (a CDK2 inhibitor). Competition with unmodified SB202190, SB203580, BIRB-796 and VX-745 decreased by 1000-fold or more the amount of phage-displayed p38 bound to the solid support, whereas neither SB202474 nor purvalanol A had a significant effect (FIG. 1B). To determine the affinity of the interactions, the amount of phage-displayed p38 bound to the solid support was quantitated as a function of test compound concentration (FIG. 1C). The binding constants measured in this manner agree well with published values (Table 2). Binding constants were averages of at least two independent experiments. Published results are $IC_{50}$'s, $K_i$'s or $K_d$'s from in vitro experiments reported in the literature, except where noted. For each published value the literature reference is shown in parentheses. These results demonstrate that the binding assay correctly discriminates between compounds that bind to the kinase, and those that do not, and yields accurate binding constants.

TABLE 1

Kinase Inhibitors

| Inhibitor | Primary Targets | Chemical Structure |
| --- | --- | --- |
| Staurosporine | Pan-inhibitor | 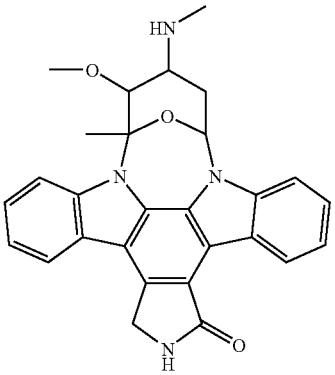 [SMILES: CNC1CC2OC(C)(C1OC)n1c3ccccc3c3c4c(c5c6ccccc6n2c5c31)C(=O)NC4] |

TABLE 1-continued

Kinase Inhibitors

| Inhibitor | Primary Targets | Chemical Structure |
|---|---|---|
| SB202190 | p38α | 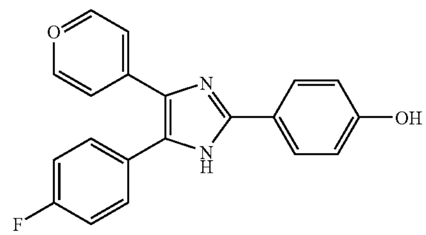 |
| SB203580 | p38α | 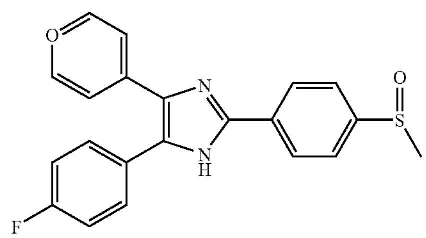 |
| VX-745 | p38α | 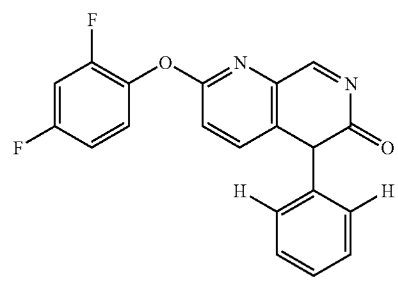 [SMILES: O=C1N=Cc2nc(Oc3ccc(F)cc3F)ccc2C1c1ccccc1] |
| BIRB-796 | p38α | 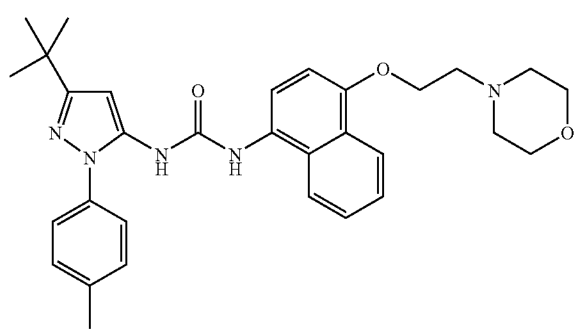 [SMILES: Cc1ccc(-n2nc(C(C)(C)C)cc2NC(=O)Nc2ccc(OCCN3CCOCC3)c3ccccc23)cc1] |
| CC-401 | JNK | 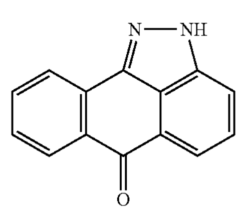 [SMILES: O=C1c2ccccc2-c2n[nH]c3cccc1c23] |

TABLE 1-continued

| Kinase Inhibitors | | |
|---|---|---|
| Inhibitor | Primary Targets | Chemical Structure |
| Gleevec | ABL | |
| Iressa | EGFR | |
| Tarceva | EGFR | |
| CI-1033 | EGFR subfamily | |

TABLE 1-continued
Kinase Inhibitors
| Inhibitor | Primary Targets | Chemical Structure |
|---|---|---|
| GW-2016 | EGFR, ERBB2, ERBB4 | 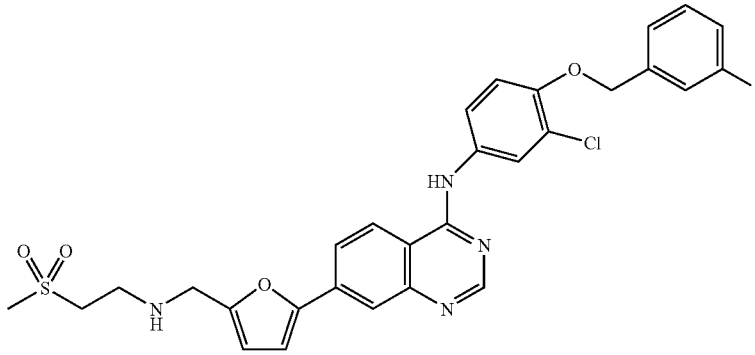 |
| EKB-569 | EGFR, ERBB2 | 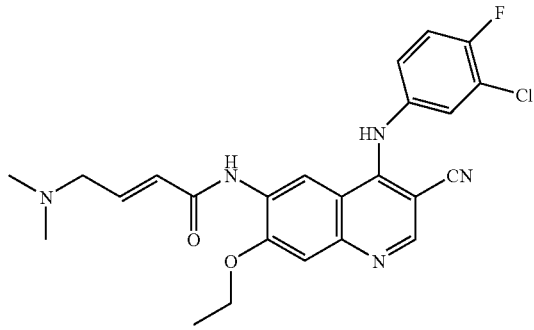 [SMILES: CCOc1cc2ncc(C#N)c(Nc3ccc(F)c(Cl)c3)c2cc1NC(=O)/C=C/CN(C)C] |
| ZD-6474 | VEGFR2, EGFR | 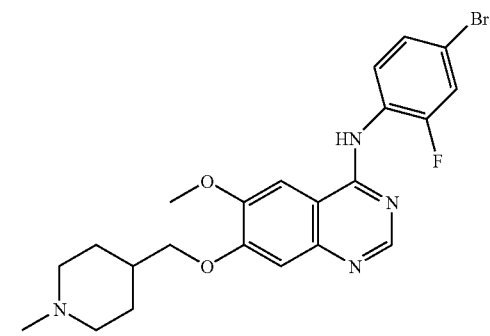 [SMILES: COc1cc2c(Nc3ccc(Br)cc3F)ncnc2cc1OCC1CCN(C)CC1] |
| Vatalanib/PTK-787 | VEGFR2 | 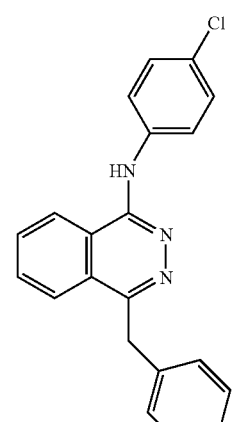 |

TABLE 1-continued

Kinase Inhibitors

| Inhibitor | Primary Targets | Chemical Structure |
|---|---|---|
| SU11248 | VEGFR2, PDGFR, FLT3 | 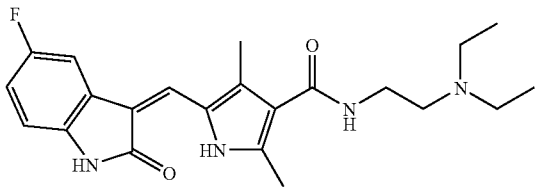 [SMILES: CCN(CC)CCNC(=O)c1c(C)[nH]c(/C=C2\C(=O)Nc3ccc(F)cc32)c1C] |
| MLN-518 | FLT3 | 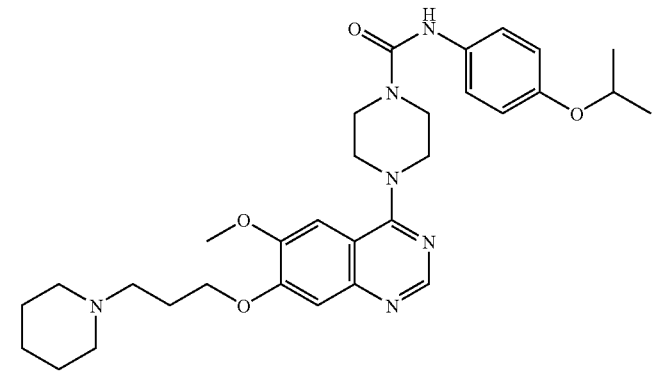 [SMILES: COc1cc2c(N3CCN(C(=O)Nc4ccc(OC(C)C)cc4)CC3)ncnc2cc1OCCCN1CCCCC1] |
| Roscovitine/CYC202 | CDK2 | 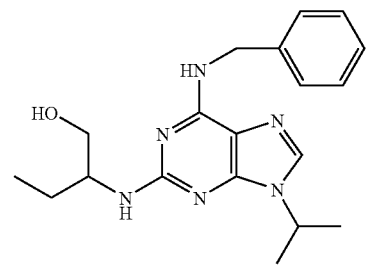 [SMILES: CCC(CO)Nc1nc(NCc2ccccc2)c2ncn(C(C)C)c2n1] |
| Flavopiridol | CDK1, CDK2, CDK4 | 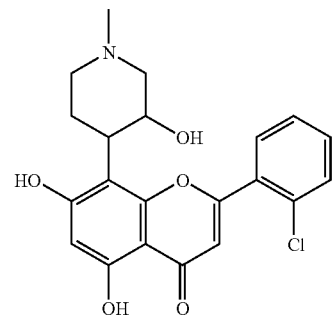 [SMILES: CN1CCC(c2c(O)cc(O)c3c(=O)cc(-c4ccccc4Cl)oc23)C(O)C1] |

TABLE 2

Comparison of binding constants measured in the competition binding assay to published results.

| Compound | Kinase | $K_d$ (nM) | Published (nM) |
|---|---|---|---|
| SB202190 | p38α | 13 | 37 (B. Frantz et at., Biochemistry 37, 13846 (1998)). |
| SB203580 | p38α | 17 | 40 (B. Frantz et al., Biochemistry 37, 13846 (1998)) |
| VX-745 | p38α | 3.2 | 0.8 C. (E. Fitzgerald et al., Nature Struct. Biol. 10, 764 (2003)) |
| BIRB-796 | p38α | 0.24 | 0.1 (C. Pargellis et al., Nature Struct. Biol. 9, 268 (2002)) |
| CC-401 | JNK2 | 84 | 110 (Z. Han et al., J. Clin. Invest. 108, 73 (2001)) |
| Gleevec | ABL | 2.2 | 37† (T. Schindler et al., Science 289, 1938 (2000)) |
| Gleevec | PDGFRβ | 28 | 50 (J. Zimmermann, E. Buchdunger, H. Mett, T. Meyer, N. B. Lydon, Bioorg. Med. Chem. Lett. 7, 187 (1997)) |
| Iressa | EGFR | 1.8 | 2.1 (A. E. Wakeling et al., Cancer Res. 62, 5749 (2002)) |

TABLE 2-continued

Comparison of binding constants measured in the competition binding assay to published results.

| Compound | Kinase | $K_d$ (nM) | Published (nM) |
|---|---|---|---|
| Tarceva | EGFR | 1.4 | 2.7 (J. D. Moyer et al., Cancer Res. 57, 4838 (1997)) |
| CI-1033 | EGFR | 1.4 | 0.8 (L. F. Allen, P. F. Lenehan, I. A. Eiseman, W. L. Elliott, D. W. Fry, Semin. Oncol. 29, 11 (2002)) |
| CI-1033 | ERRB2 | 8.4 | 19 (L. F. Allen, P. F. Lenehan, I. A. Eiseman, W. L. Elliott, D. W. Fry, Semin. Oncol. 29, 11 (2002)) |
| GW-2016 | EGFR | 5.5 | 11 (D. W. Rusnak et al., Mol. Cancer Ther. 1, 85 (2001)) |
| GW-2016 | ERBB2 | 11 | 9.2 (D. W. Rusnak et al., Mol. Cancer Ther. 1, 85 (2001)) |
| EKB-569 | EGFR | 1.0 | 38 (C. J. Torrance et al., Nature Med. 6, 1024 (2000)) |
| ZD-6474 | EGFR | 17 | 500 (S. R. Wedge et al., Cancer Res. 62, 4645 (2002)) |
| ZD-6474 | VEGFR2 | 470 | 40 (S. R. Wedge et al., Cancer Res. 62, 4645 (2002)) |
| Vatalanib | VEGFR2 | 70 | 37 (J. M. Wood et al., Cancer Res. 60, 2178 (2000)) |
| SU11248 | VEGFR2 | 0.23 | 9 (D. B. Mendel et al., Clin. Cancer Res. 9, 327 (2003)) |
| SU11248 | PDGFRβ | 0.21 | 8 (D. B. Mendel et al., Clin. Cancer Res. 9, 327 (2003)) |
| MLN-518 | FLT3 | 3.5 | 220‡ (L. M. Kelly et al., Cancer Cell 1, 421 (2002)) |
| Roscovitine | CDK2 | 2900 | 700(L. Meijer et al., Eur. J. Biochem. 243, 527 (1997)) |
| Flavopiridol | CDK2 | 200 | 100 (B. A. Carlson, M. M. Dubay, E. A. Sausville, L. Brizuela, P. J. Worland, Cancer Res. 56, 2973 (1996)) |

†Measured at [ATP] = 0.5 mM
‡Determined in a cell-based assay

To compete with the interaction between immobilized SB202190 and phage-displayed p38, compounds must either bind directly at the ATP site, or allosterically alter its conformation. Both modes of action are observed. SB203580 is known to bind directly in the ATP site, while BIRB-796 binds predominantly in an adjacent position and indirectly affects the conformation of the ATP site. Both compounds are known potent inhibitors of p38. Furthermore, it is known that the binding of BIRB-796 requires a specific conformational change in the p38 protein that results in very slow association kinetics, while SB202190 binding does not require this conformational change and is fast. The competition binding assay yielded accurate binding constants for both compounds (Table 2), and the distinct binding kinetics for BIRB-796 and SB202190 are also observed in the competition assays. The detailed behavior of the kinase is therefore faithfully recapitulated by the phage-displayed p38 protein.

All references cited herein are hereby incorporated by reference in their entireties, whether previously specifically incorporated or not. As used herein, the terms "a", "an", and "any" are each intended to include both the singular and plural forms unless it is inappropriate in context.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. A method for identifying a test molecule that binds to a phage-displayed polypeptide, wherein the test molecule is not previously known to bind to the phage-displayed polypeptide, the method comprising:
(a) contacting a reference moiety with the phage-displayed polypeptide in the presence and absence of test molecule, wherein the reference moiety is immobilized on a solid support, wherein the reference moiety is known to bind to the phage-displayed polypeptide and further wherein the phage-displayed polypeptide is a kinase polypeptide, and reference moiety binds to an ATP site of the kinase polypeptide;
(b) further wherein (i) binding of the phage-displayed polypeptide to the reference moiety occurs if the test molecule does not bind to the phage-displayed polypeptide, and wherein (ii) non-binding of the phage-displayed polypeptide to the reference moiety occurs if the test molecule does bind to the phage-displayed polypeptide;
(c) removing unbound phage-displayed polypeptide; and
(d) detecting phage-displayed polypeptide bound to the immobilized reference moiety in step (b);
whereby a decrease in an amount of phage-displayed polypeptide bound to the immobilized reference moiety contacted in the presence of the test molecule as compared to an amount of phage-displayed polypeptide bound to the immobilized reference moiety in the absence of the test molecule identifies the test molecule as a binder of the phage-displayed polypeptide.

2. The method of claim 1, wherein the presence of the phage displaying the phage-displayed polypeptide is detected by quantitative polymerase chain reaction (qPCR).

3. The method of claim 1, further comprising quantifying the amount of phage displaying the phage-displayed polypeptide bound to the immobilized reference moiety.

4. The method of claim 3, wherein the quantifying is by qPCR, phage plaque assay or fluorescence polarization.

5. The method of claim 1, wherein the reference moiety is purvalanol B, SU5402, SU6668, PD-173955, SB202190, staurosporine, SB203580, VX-745, BIRB-796, CC-401, imatinib mesylate, gefitinib, erlotinib, CI-1033, GW-2016, EKB-569, ZD-6474, vatalanib/PTK-787, SU11248, MLN-518, roscovitine/CYC202, or flavopiridol.

6. The method of claim 1, wherein the protein kinase polypeptide is MAPK12, MAP2K6, GPRK7, CDK7, CDK9, PCTK1, JNK1α/MAPK8α, JNK1β3/MAPK8β, JNK2a/MAPK9a, JNK3/MAPK10, CDK2, DAPK2, DMPK, NEK2, PAM, PAK6, KIAA1048, STK16, RS6KA2, RS6KA3, RS6KA5, LCK, PRKAA2, CSK, DAPK3, PRKACA, murine PAM, PAK3, PAK7, BIKE, murine STK3, STK4, STKI5/STK6(BTAK)/AURORA2, PIMI, PIM2, CAMK1, LOC57118 (CamK1-like), CamKIG, CamK2A, CamK2B, CamK2D, CamK2G, CamKKI, CamKK2, FGFR1, PDGFRβ, casein kinase 1, gamma 1, MAPK14/p38, STK18, STK25, VEGFR2, ABL, ABL mutants, BRAF, BRAF mutants, EGFR, EGFR mutants, ERBB2, ERBB4, p38α, FLT3, CDK1, or CDK4.

7. The method of claim 1, further comprising determining the concentration of the test molecule at which about 50% of the phage-displayed polypeptide are bound to the reference moiety relative to the amount bound in the absence of the test molecule, wherein the concentration at which 50% of the phage-displayed polypeptide are bound to the reference moiety is the value of the dissociation constant ($K_d$) of the phage-displayed polypeptide.

8. The method of claim 1, wherein the solid support is a bead.

9. The method of claim 8, wherein the bead is in a column or a well of a multi-well plate.

10. The method of claim 1, wherein the solid support is a well of a multi-well plate.

11. A method for identifying whether a test molecule binds to more than one member of a group of different phage-displayed polypeptides, wherein the test molecule is not previously known to bind to more than one member of the group of phage-displayed polypeptides, the method comprising:
  (a) contacting, in a single well, a group of different phage-displayed polypeptides with a reference moiety in the presence and absence of a test molecule, wherein the reference moiety is immobilized on a solid support and wherein the reference moiety is known to bind to the group of phage-displayed polypeptides, said polypeptides being phage-displayed protein kinases and the reference moiety binding to an ATP site of each phage-displayed protein kinase polypeptide, and wherein the test molecule is tested for binding to one or more members of the group of phage-displayed polypeptides;
  (b) further wherein (i) binding of a phage-displayed polypeptide to the reference moiety occurs if the test molecule does not bind to the phage-displayed polypeptide, and wherein (ii) binding of the phage-displayed polypeptide to the reference moiety does not occur if the test molecule does bind to the phage-displayed polypeptide;
  (c) removing the unbound phage-displayed polypeptides from a mixture of step (b); and
  (d) detecting the presence of each member of the group of phage-displayed polypeptides bound to the immobilized reference moiety after removing the unbound phage-displayed polypeptides;
  whereby decreases in the amounts of binding of more than one member of the group of phage-displayed polypeptides to the immobilized reference moiety in the presence of the test molecule as compared to the absence of the test molecule identifies the test molecule as a binder of more than one member of the group of phage-displayed polypeptides.

12. The method of claim 11, wherein the presence of each member of the group of phage-displayed polypeptides is detected by qPCR.

13. The method of claim 11, further comprising quantifying the amount of each member of the group of phage-displayed polypeptides bound to the immobilized reference moiety.

14. The method of claim 13, wherein the quantifying is by qPCR, phage plaque assay or fluorescence polarization.

15. The method of claim 11, wherein the reference moiety is purvalanol B, SU5402, SU6668, PD-173955, SB202190, staurosporine, SB203580, VX-745, BIRB-796, CC-401, imatinib mesylate, gefitinib, erlotinib, CI-1033, GW-2016, EKB-569, ZD-6474, vatalanib/PTK-787, SU 11248, MLN-518, roscovitine/CYC202, or flavopiridol.

16. The method of claim 11, wherein the protein kinase polypeptides are independently selected from the group consisting of MAPK12, MAP2K6, GPRK7, CDK7, CDK9, PCTK1, JNK, JNK1α/MAPK8α, JNKIβ3/MAPK8β, JNK2a/MAPK9a, JNK3/MAPK10, CDK2, DAPK2, DMPK, NEK2, PAM, PAK6, KIAA1048, STK16, RS6KA2, RS6KA3, RS6KA5, LCK, PRKAA2, CSK, DAPK3, PRKACA, murine PAM, PAK3, PAK7, BTKE, murine STK3, STK4, STK15/STK6(BTAK)/AURORA2, PIMI, PIM2, CAMK1, LOC57118 (CamK1-like), CamKIG, CamK2A, CamK2B, CamK2D, CamK2G, CamKKI, CamKK2, FGFR1, PDGFRβ, casein kinase 1, gamma 1, MAPK14/p38, STKI8, STK25, VEGFR2, ABL, ABL mutants, BRAF, BRAF mutants, EGFR, EGFR mutants, ERBB2, ERBB4, p38α, FLT3, CDK1, and CDK4.

17. The method of claim 11, wherein the solid support is a bead.

18. The method of claim 17, wherein the bead is in a column or a well of a multi-well plate.

19. The method of claim 11, wherein the solid support is a well of a multi-well plate.

20. The method of claim 1, wherein the reference moiety is a small molecule.

21. The method of claim 11, wherein the reference moiety is a small molecule.

22. The method of claim 1, wherein said phage-displayed polypeptide is present as a homogeneous group of phage-displayed polypeptides.

* * * * *